United States Patent [19]

Wolf, Jr. et al.

[11] 4,385,629

[45] May 31, 1983

[54] PORTABLE EMERGENCY RESPIRATORY SYSTEM

[76] Inventors: E. George Wolf, Jr., 4730 Whitewood Ct.; Charles E. Cox, 4333 Rosegarden Ct., both of Dayton, Ohio 45424

[21] Appl. No.: 234,053

[22] Filed: Feb. 12, 1981

[51] Int. Cl.³ .............................................. A61M 25/00
[52] U.S. Cl. .................................. 128/207.14; 128/912
[58] Field of Search ...................... 128/202.28, 207.14, 128/207.15, 910, 205.13, 205.17, 205.18, 205.19, 205.24, 204.25, 200.18, 203.11, 203.28, 203.29, 207.16, 205.12, 205.25

[56] References Cited

U.S. PATENT DOCUMENTS

| | | | |
|---|---|---|---|
| 3,297,027 | 1/1967 | Rusch | 128/202.28 |
| 3,827,729 | 8/1974 | Kamen | 128/207.14 |
| 3,993,059 | 11/1976 | Sjostrand | 128/207.16 |
| 4,030,492 | 6/1977 | Simbruner | 128/205.24 |
| 4,109,651 | 8/1978 | Steigerwald | 128/205.24 X |
| 4,112,940 | 9/1978 | Parkes | 128/910 |
| 4,244,363 | 1/1981 | Moore, Jr. et al. | 128/205.17 |

FOREIGN PATENT DOCUMENTS 2213764  9/1973  Fed. Rep. of Germany ...... 128/910

*Primary Examiner*—Henry J. Recla
*Attorney, Agent, or Firm*—Donald J. Singer; Arthur R. Parker

[57] ABSTRACT

Utilization of a standard, portable oxygen tank and regulator in an emergency respiratory system including an endotracheal adaptor in fluid communication with the regulator and having a first, flexible tube insertable in the windpipe of a patient undergoing emergency treatment, and a second flexible, manually-operable tube attached to the adaptor in opposed relation to the first tube and compressible to direct the oxygen flowing between the regulator and adaptor into the patient's lungs by way of the first tube.

6 Claims, 2 Drawing Figures

PORTABLE EMERGENCY RESPIRATORY SYSTEM

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

This invention relates generally to the field of portable oxygen breathing apparatus and, in particular, to the conversion of a portable oxygen cylinder and regulator into an emergency respiratory system.

2. Description of the Prior Art

Various types of both non-portable and portable oxygen breathing equipment have been designed and/or used for many decades for the purpose of either prescribed, preplanned medical treatment, for emergency situations and/or for various recreational, commercial, and/or research and development activities. Such apparatus has also been in operational use in hyperbaric and high altitude chambers, and in aircraft as well. In this connection, the following U.S. patents have been examined for relevancy to the present invention. Firstly, U.S. Pat. No. 980,996, issued Jan. 10, 1911 to D. E. Parker, is an example of the non-portable-type in which a combined oxygen generator and oxygen administering device employs so-called "oxone briquets" which react with water in a chamber to produce oxygen. After being transferred from the chamber and washed for impurities, the oxygen is exhausted through an outlet pipe into a flexible hose and mouthpiece adapted to be placed over the nose and mouth of the victim or patient. An air pump consisting of a flexible bulb and tube is used to increase the supply of oxygen to the user by increasing the air pressure in a surrounding chamber and thus increase the amount of water fed upward through a perforated diaphragm supporting the oxone briquets. In a second U.S. Pat. No. 1,177,208, issued Mar. 28, 1916 to J. H. Pierpont, a portable type of oxygen or air-breathing apparatus called a "pulmotor" is used. A reservoir bag of oxygen is suspended from the neck of the operator, and a pneumatic bag is attached between his arm and side. A first tube is disposed between the bag and reservoir, and a second tube extends between the bag and a valve device held in one hand of the operator. In fluid communication with the second tube is a metal tube that is held in the same hand and at the end of which is a third flexible tube that is, in turn, attached to a face mask. In operation, the pneumatic bag is compressed between the arm and side of the operator, causing a valve in the hand held valve device to open fluid communication between the second tube and the metal tube to thereby direct flow to the face mask.

A pair of additional U.S. patents; namely, U.S. Pat. No. 2,912,982, issued Nov. 17, 1959 to A. J. Barsky, and U.S. Pat. No. 3,338,705, issued June 18, 1968 to S. L. Grosshandler, both teach improved types of endotracheal tube adaptors. The Barsky device relates to a rigid adaptor and flexible tube collectively shaped in the form of a question mark and which principally involves improved joint means connecting the rigid adaptor to a flexible tube, this joint connection being of the "slip-joint" type to enable its simple connection or separation merely by pushing or pulling. Also, an opening to the interior of the adaptor is provided through which is fed a suction tube which also leads through the endotracheal tube for insertion into the windpipe to extract mucus, blood or other fluids accumulated therein. In U.S. Pat. No. 3,388,705, details of an adaptor are described for attaching endotracheal tubes to an anesthesia machine. At one end thereof the adaptor incorporates a molded tubular body with a tapered sleeve engaged within a female connector on the chimney of an anesthesia machine. At its other end, the adaptor uses an integral flexible diaphragm incorporating an axial opening through which one end of the endotracheal tube is inserted. The diameter of the adaptor-axial end opening is made smaller than that of the endotracheal tube thereby ensuring a relatively tight hold therebetween.

In another U.S. Pat. No. 3,017,880, issued Jan. 23, 1962 to M. H. Brook, a resuscitator is disclosed that consists generally of a flexible tube insertable in the patient's mouth and beyond to a position nearly adjacent the pharynx, with a mouthguard located in position to overlie the patient's mouth. Again, a suction tube is employed and details of the connection between a primary tube and the flexible tube are described. The final two patents listed herein; namely, U.S. Pat. No. 3,461,877 issued Aug. 19, 1969 to E. T. Morch and U.S. Pat. No. 3,794,030, issued Feb. 26, 1974 to H. N. Cotabish et al, are included respectively to show the teaching of a tracheotomy tube construction, and another illustration of an oxygen generator. In the former, seen in U.S. Pat. No. 3,461,877, a tracheotomy tube is illustrated in combination with a supply of oxygen or more accurately, a supply of air furnished through the use of a respirator with an exhalation value unit and a pair of air hoses, one of which connects the respirator to the valve and the second connecting the valve unit to the tracheotomy tube. Lastly, U.S. Pat. No. 3,794,030 again shows a device for both the generation and administering of oxygen, as was the case with the initially discussed U.S. Pat. No. 980,996. In this case, however, instead of the older use of oxone briquets, there is a canister containing carbon dioxide absorbing and an oxygen producing chemical, such as potassium superoxide. A flexible breathing hose with a mouthpiece is attached to the outlet port of the canister.

Although the present invention makes use of known components, such as the endotracheal adaptor and tube, as well as other flexible-type tubing and oxygen hoses, and such elements are obviously taught per se in the prior art as may be represented in the above-outlined patents; nevertheless, the present invention specifically relates to an emergency respiratory system utilizing many of the components described in the cited patents in a new and improved arrangement that includes the use of a pressurized supply of oxygen and, in addition, a novel and simplified passive-type technique for insuring the application of a positive pressure flow of oxygen to the lungs of the patient or victim, as will readily appear hereafter in the following summary and detailed description.

SUMMARY OF THE INVENTION

The present invention consists briefly of an emergency respiratory system that may easily be adapted for use with a standard type of oxygen cylinder and regulator by combining therewith a standard endotracheal adaptor unit made with a substantially T-shaped configuration forming a leg segment, and oppositely disposed arm segments, all incorporating interior, communicating fluid passages. One end of any standard-type of flight or other oxygen hose may be attached to the leg of the "T" and the other end thereof is adaptable to be attached, for example to the pressure regulator of a standard portable-type oxygen tank or cylinder. A standard endotracheal tube or esophageal airway is attached to one arm segment of the "T", with its opposite end insertable in the trachea or windpipe, or esophagus respectively of the patient or victim being treated. In the standard endotracheal adaptor unit of this configuration, the opposite arm segment is normally capped or closed off, leaving the leg segment and the endotracheal tube-attached arm segment as the only openings incorporated therewithin. However, in the present arrangement, the other arm segment is formed with an open end to which is attached a flexible tubing for the express purpose of providing a unique and yet simplified control of the pressurized oxygen flowing into the endotracheal adaptor and tube by way of the oxygen hose and leg segment. A more detailed description of the present emergency respiratory system will be set forth hereinbelow in the following disclosure, taken in connection with the accompanying drawings, in which:

DESCRIPTION OF THE PREFERRED EMBODIMENT

Figure 1:
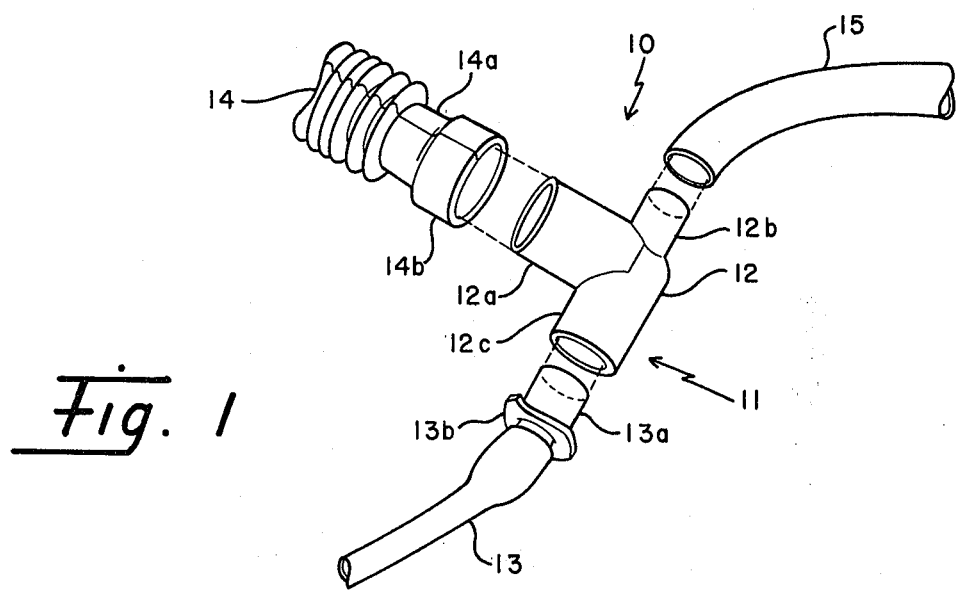
FIG. 1 is a partly schematic, exploded and perspective view, illustrating the principal components of the basic form of the emergency respiratory system of the invention.

Referring generally to the drawings and, in particular, to FIG. 1 thereof, the new and improved emergency respiratory system of the present invention is indicated generally at 10 as including the principal components of a hollow, endotracheal adaptor unit indicated generally at 11, a standard flight oxygen hose, shown broken away at 14, an endotracheal tube 13, and a flexible tube at 15. The said endotracheal adaptor unit 11 is of a standard type and consists of a main body portion 12 of a substantially T-shaped configuration to thereby specifically provide an intermediately-disposed leg segment 12a and a pair of oppositely-disposed arm segments 12b and 12c extending at approximately right angles to said leg segment 12a. Each of the said leg, and arm segments 12a, and 12b and 12c, respectively, serve a two-fold purpose. Firstly, they act as a fitting means for the respective attachment thereto of the previously-referred to principal components of the invention, as will be described hereinafter in more detail. Secondly, because of the hollow configuration thereof, there is naturally incorporated a continuous, relatively elongated fluid passage that extends between the opposite arm segments 12b and 12c that communicates with another, relatively short fluid passage naturally formed in the leg segment 12a. As is self-evident from examination of both figures of the drawings, the diameter of arm segment 12c is relatively enlarged as compared to that of arm segment 12b. Moreover, the diameter of the leg segment 12a is made of a somewhat larger diameter than that of the arm segment 12c. This arrangement is used to ensure that the various fittings incorporated in the said endotracheal adaptor unit 11 are made compatible with available standard-size hoses and tubes considered to be preferable for use with the present apparatus.

Again referring to FIG. 1, it is clearly seen that, to the arm segment/fitting 12c of the endotracheal adaptor unit 11, is attached one end of the endotracheal tube 13. For this purpose, the latter component is formed with a fitting element 13a on one end thereof, which end-fitting element 13a interfits within the end opening of the arm segment 12c. To provide a proper interconnection therebetween, the outside diameter of the end-fitting element 13a is made just small enough to interfit in a relatively snug-fit relation within the opening of the relatively enlarged, inside diameter of the arm segment-fitting 12c. A peripherally-disposed flange 13b formed on the fitting element 13a at the location illustrated, acts as a stop means to limit the distance of insertion of the appropriate end of the endotracheal tube 13 within the endotracheal adatpor unit 11. Of course, it is the opposite end of the endotracheal tube 13 that is inserted into the patient's trachea or windpipe, or esophageal airway.

Figure 2:
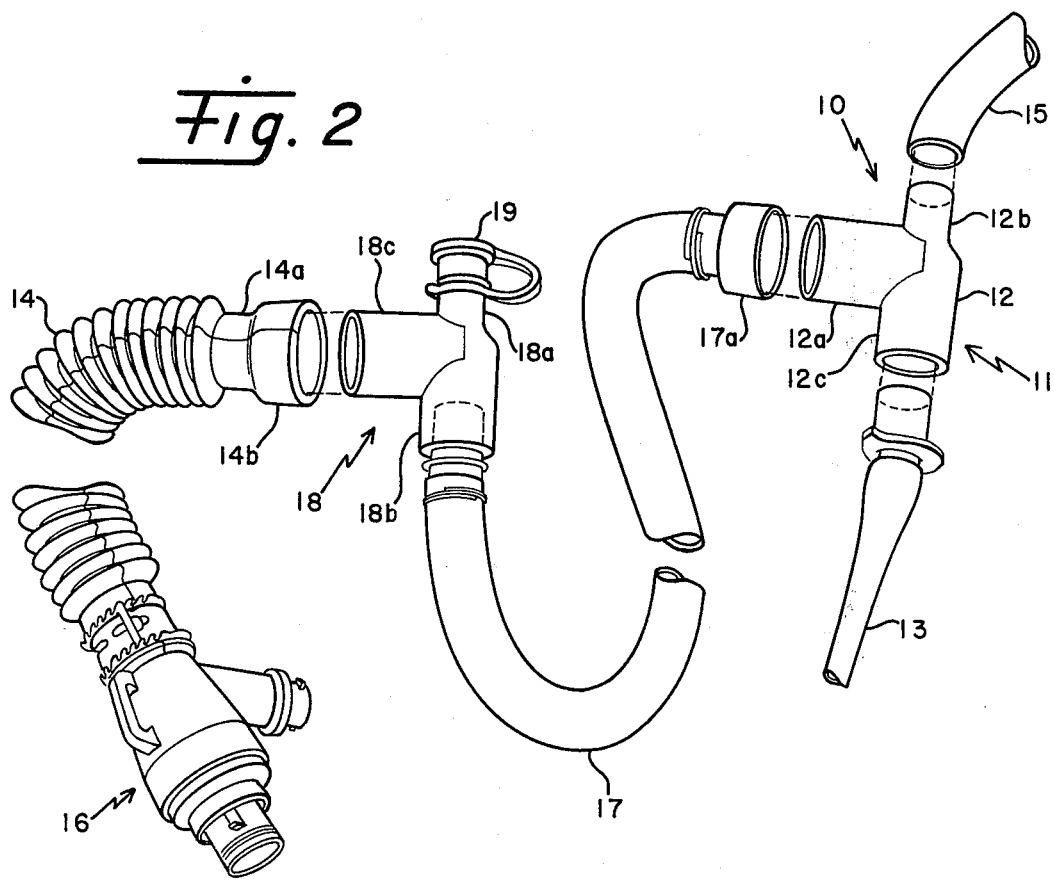
FIG. 2 is a second view, similar to FIG. 1, but showing further details of the inventive respiratory system including the addition of an extension hose.

To supply the pressurized oxygen needed to inflate the victim's or patient's lungs, the previously-referred to standard flight oxygen hose 14 is attached to the endotracheal adaptor unit 11 through the application of an extension piece 14a integrally formed on one end of the hose 14. Said extension piece 14a is, additionally, provided with a resilient, relatively enlarged end portion, at 14b, that engages in a relatively tight-fitting relation over the end of the combined fitting and leg segment 12a. As seen particularly in FIG. 2, the opposite end of the flight oxygen hose 14 may be equipped with a standard adaptor unit, indicated generally at 16, which is used to interconnect the hose 14 with the pressure regulator of a standard, portable-type oxygen cylinder. The cylinder and regulator are not shown, since the specific details thereof are unimportant to the present invention. Suffice to say is that, as a matter of convenience and for the purpose of providing a suitable pressurized source of oxygen, the primary use contemplated for the present invention is with both the non-fighter-type of military aircraft and in connection with activities involving the use of both altitude and hyperbaric chambers. In this regard, the standard oxygen cylinder involved with the present invention utilizes a pressure of approximately 450 lbs per square inch (psi) when fully charged. Upon adjustment of its pressure regulator valve to the "emergency" setting, this pressure is reduced to about 40 psi. It is this 40 psi pressure with which the oxygen flows into the flight hose line 14, from whence it enters the communicating fluid passages formed in the leg segment 12a and between arm segments 12b, 12c of the endotracheal adaptor unit 11. It is to be emphasized that the component 14 is described as a "flight" oxygen hose only for the purpose of an example. Any other suitable type oxygen hose may be used without departing from the true spirit or scope of the invention.

Again referring to FIG. 2, the inventive apparatus may be somewhat modified to facilitate its application to personnel in need by providing greater flexibility through the use of an extension fluide line at 17. The latter element 17 is interposed between the hose 14 and the endotracheal adaptor unit 11. As in the case of the hose 14, extension line 17 is equipped with an enlarged, combined fitting and opening portion 17a on one end thereof. The inside diameter thereof is specifically dimensioned to engage in a tight-fitting relation over the leg segment 12a of the endotracheal adaptor unit 11.

The other end of extension line 17 is shown interconnected with the hose 14 through the use of another endotracheal adaptor-type unit, indicated generally at 18. Although of an identical T-shaped configuration as that previously-described for the endotracheal adaptor unit 11, since it is not used for the same endotracheal function, the element 18 will be hereinafter identified merely as a connector. Said connector 18 also includes a pair of arm portions at 18a and 18b, and, as shown, a leg portion 18c disposed substantially at right angles thereto. As described before, again, the previously-noted enlarged end portion 14b of the extension piece 14a integrally formed on the end of the hose 14 is attached in a relatively tight-fitting relation over the aforementioned leg portion 18c of the connector 18. Moreover, the other end of the extension line 17 is positioned in a snug-fitting relation within the opening provided therefor by the relatively enlarged-diameter arm portion 18b, as illustrated in the said FIG. 2. To complete the assembly of the connector 18, a cap element 19 is used as shown to seal off and thus prevent the loss of oxygen through the otherwise opened end of the arm portion 18a.

In operation of the present emergency respiratory system, a uniquely positioned and yet simplified, passive-type of control means is utilized with the endotracheal adaptor unit 11 (see FIG. 1, for example) for ensuring that the oxygen flow is directed in a positive manner into the victim's or patient's lungs. For this express purpose, an open-ended, flexible tube, indicated at 15, is used by being attached in a tight-fitting relation over the end of the relatively reduced-diameter arm segment 12b of the endotracheal adaptor unit 11. With this arrangement, after inserting the free end of the endotracheal tube 13 normally through the mouth of the victim or patient to be treated so that it is positioned within the trachea or windpipe, or esophageal airway the pressure regulator of the oxygen source of supply to be used therewith may then be adjusted to the "emergency" position. This action creates a flow of oxygen into the hose 14 under a positive pressure of about 40 lbs per square inch (psi), as was previously described. Thereafter, depending on whether or not the extension line 17 is used in the particular application, the pressurized oxygen is delivered to said extension line and/or directly to the fluid passage formed by the leg segment 12a of the endotracheal adaptor unit 11. At this time, if no action has as yet been applied to the tube 15, the flow of oxygen will naturally take the path of least resistance; i.e. it will flow into the continuous fluid passage extending between the arm segments 12b and 12c and then will exhaust out through the arm segment 12b and the open end of the tube 15.

To initiate therapy of the patient or introduce life-giving oxygen to the non-breathing victim of a crisis situation, it is only necessary to apply manual pressure to collapse the tube 15 thereby automatically choking off the flow of oxygen therethrough and, at the same time, force or, in other words, positively redirect the oxygen flow in the opposite direction within the endotracheal adaptor unit 11 through the endotracheal tube 13 for its admission into, and inflating the patient's or victim's lungs. Because of the combined use of a pressurized source and the manually operable tube 15, there is ensured the flow of a positive pressure oxygen in the opposite direction because it will naturally seek and take the path of least resistance. In accordance with acceptable medical practice, the admission of pressurized oxygen into the lungs should be performed at a cyclic rate of approximately twelve times per minute to naturally enable periodic, induced breathing to occur and to exhaust any excess oxygen and, or course, carbon dioxide from the lungs. To accomplish the recommended inhalation and expiration or exhalation functions, it is only necessary to periodically collapse and release the manually applied pressure on the tube 15. On collapsing it, as was noted hereinbefore, the positive pressure oxygen will automatically flow into and inflate the lungs. On release of this pressure, which action allows the flexible tube 15 to expand or return to its original, non-compressed condition, both the oxygen still incoming from the hose 14, and the oxygen and carbon dioxide within the lungs at this time will automatically exhaust out through the now-opened tube 15. This latter action is ensured because the opening of the tube 15 to allow the still-incoming oxygen to flow therethrough will rather quickly reduce the atmospheric pressure within the fluid passage between the arm segments 12b and 12c and also the endotracheal tube 13 below that of the relatively higher atmospheric pressure existing within the lungs, which higher pressure will naturally force the flow of oxygen and carbon dioxide out of the lungs. Thus, the foregoing arrangement involving a standard T-shaped endotracheal adaptor unit 11 that is modified as described hereinbefore, to incorporate the manually-operable, flexible tube 15, ensures the passive control and direction of a relatively high pressure oxygen flow into the patient's or victim's lungs through the simple compression of the said tube 15. In other words, the maintenance of a single manual compression of the tube 15 is all that is required to initially inflate the lungs. Thereafter, it is only necessary to periodically release and reapply the compression step at the accepted cyclic rate established by medical practice to reinflate and exhaust the gases within the lungs for the necessary breathing function.

Although the novel apparatus of the present invention has been described in connection with the use of a portable oxygen tank and regulator for the purpose of oxygen therapy and to treat compromised, non-breathing patients or victims at locations where 100% oxygen is not readily available, it is obvious that the present apparatus is of a more general utility and may clearly be employed in areas where 100% oxygen is available to treat victims of heart attacks, neurological decompression, air embolus and the like. In either event, in the case of the use of either the portable or non-portable oxygen supply, the single step operation of the passive control-tube 15 of the present arrangement, where all that is required is a single squeeze for each pumping action of the pressurized oxygen into the lungs, offers a simplified and clear advantage over the standard "ambu" bag in current use. This is an inflatable bag that is required to be continually squeezed to provide the necessary pressurization to the oxygen being used for lung inflation, oftentimes with the use of both hands of the operator to achieve the desired pressure.

We claim:

1. An emergency respiratory system for administering oxygen therapy and treating an individual in respiratory failure, comprising: an endotracheal adaptor unit having a fluid passage; an endotracheal tube attached to said adaptor unit and communicating with said fluid passage, said endotracheal tube insertable within the windpipe, trachea, or esophageal airway of an individual undergoing treatment; pressurized oxygen delivery means attached to said adaptor unit and communicating with said fluid passage for introducing relatively high pressure oxygen into said fluid passage; and pressure-applying and directing means attached to said adaptor unit and communicating with and providing a continuation of said fluid passage away from that of said endotracheal tube, said last-named means including a single flexible tubing having one end attached to said adaptor unit and the other end opening to the atmosphere, said flexible tubing being manually squeezable to a first, compressed position to shut off the flow of pressurized oxygen through the continuation of said fluid passage formed by said flexible tube and positively redirect the flow through said endotracheal tube to inflate the individual's lungs, and releasable to a second, tube-expanded condition to provide for the expiration of the lungs through the said flexible tubing.

2. In an emergency respiratory system as in claim 1, wherein said endotracheal adaptor unit includes a body portion having an intermediately-disposed leg segment and a pair of opposed arm segments, said leg and arm segments in communication with said fluid passage.

3. In an emergency respiratory system as in claim 2, wherein said leg segment constitutes a first fitting for attaching said pressurized oxygen delivery means to said endotracheal adaptor unit.

4. In an emergency respiratory system as in claim 3, wherein said arm segments comprise second and third fittings for attaching said endotracheal tube and said flexible tubing, respectively, to said endotracheal adaptor unit.

5. In an emergency respiratory system as in claim 4, wherein said pressurized oxygen delivery means includes an oxygen hose attached to said leg segment.

6. In an emergency respiratory system as in claim 5, further including an extension fluid line interposed between said oxygen hose and said leg segment.

* * * * *